US009358578B2

(12) United States Patent
Lewis et al.

(10) Patent No.: US 9,358,578 B2
(45) Date of Patent: Jun. 7, 2016

(54) PRINTING

(71) Applicant: INOVINK LIMITED, Sheffield (GB)

(72) Inventors: David Malcolm Lewis, West Yorkshire (GB); Peter Jeffrey Broadbent, North Yorkshire (GB)

(73) Assignee: INOVINK LIMITED, Sheffield (GB)

( * ) Notice: Subject to any disclaimer, the term of this patent is extended or adjusted under 35 U.S.C. 154(b) by 178 days.

(21) Appl. No.: 14/169,498

(22) Filed: Jan. 31, 2014

(65) Prior Publication Data

US 2014/0147576 A1   May 29, 2014

Related U.S. Application Data

(62) Division of application No. 12/223,783, filed as application No. PCT/GB2007/000478 on Feb. 12, 2007, now abandoned.

(30) Foreign Application Priority Data

Feb. 10, 2006  (GB) .................................. 0602821.1

(51) Int. Cl.
| *B05D 5/06* | (2006.01) |
| *B41M 3/14* | (2006.01) |
| *G01N 21/55* | (2014.01) |
| *B42D 25/29* | (2014.01) |
| *B42D 25/382* | (2014.01) |

(52) U.S. Cl.
CPC ................ *B05D 5/063* (2013.01); *B41M 3/14* (2013.01); *B42D 25/29* (2014.10); *G01N 21/55* (2013.01); *B42D 25/382* (2014.10)

(58) Field of Classification Search
None
See application file for complete search history.

(56) References Cited

U.S. PATENT DOCUMENTS

| 2,726,920 A | 12/1955 | Federkiel et al. ................. 8/515 |
| 4,266,006 A | 5/1981 | Uhlig et al. |
| 5,096,229 A | 3/1992 | Carlson .......................... 283/75 |
| 2003/0164611 A1 | 9/2003 | Schneider et al. .............. 283/57 |

FOREIGN PATENT DOCUMENTS

| DE | 1 301 249 | 8/1969 |
| EP | 1 138 743 | 10/2001 |
| FR | 1 540 858 | 9/1968 |
| GB | 1 512 018 | 5/1978 |
| GB | 2 412 350 | 9/2005 |
| JP | 3-180384 | 8/1991 |
| JP | 2000-75556 | 3/2000 |
| WO | 93/22142 | 11/1993 |
| WO | WO 2005/120847 A1 | 12/2005 |
| WO | WO 2005/121893 A1 | 12/2005 |

OTHER PUBLICATIONS

International Search Report for PCT/GB2007/000478, mailed Jun. 13, 2007.
Great Britain Search Report for GB Application No. 0602821.1, dated Jan. 29, 2007.
"Studies in Conservation", vol. 38(2), pp. 99-127, Chemical Abstract No. 119:138418, (1993).
Chemical Abstract No. 87:125320 & Bundesminist. Forsch. Technol., T 76-42, 155 pp., (1976).
Chemical Abstract No. 132:214753 & Jpn. Kokai Tokkyo, Koho, 37 pp., (2000).
Notification Concerning Transmittal of International Preliminary Report on Patentability; PCT/IB/326; International Application No. PCT/GB2007/000478; International Filing Date Feb. 12, 2007 (7 pgs).
Hans Rudolf Schweizer; "Kunstliche Organische Farbstoffe Und Ihre Zwischenprodukte"; *Springer, Verlag*, pp. 245-246 (1964).

*Primary Examiner* — Bruce H Hess
*Assistant Examiner* — Christopher Polley
(74) *Attorney, Agent, or Firm* — Nixon & Vanderhye P.C.

(57) ABSTRACT

An image article comprises a substrate having a security image coated on at least a portion thereof, which security image effects less than 50% reflectance of radiation of a wavelength between 800 and 900 nm, wherein the security image comprises a defined infrared-absorbing compound, for example Pigment Green 8, wherein said infrared-absorbing compound does not create a strongly colored security image.

11 Claims, No Drawings

PRINTING

This application is a divisional of patent application Ser. No. 12/223,783 filed Nov. 26, 2008, pending, which is a 371 of PCT/GB2007/000478, filed Feb. 12, 2007, which claims priority to British Patent Application No. 0602821.1 filed Feb. 10, 2006, the entire contents of each of which are hereby incorporated by reference.

FIELD OF THE INVENTION

This invention relates to methods of manufacturing image articles, and image articles per se.

BACKGROUND OF THE INVENTION

Image articles comprising security images are well known. Security images generally comprise an image which is invisible or undetectable under ambient conditions, and which can be rendered visible or detectable by application of a suitable stimulus; or alternatively, the image may change from one colour under ambient conditions to another colour upon application of a stimulus.

Security images may be manufactured by coating security inks or compounds onto a substrate. Examples of known compounds which when coated onto a substrate provide a security image include photochromic compounds which generally change from colourless to coloured upon the application of ultraviolet light, and thermochromic compounds which generally change from colourless to coloured upon the application of heat.

Image articles which include security images are useful in many areas of industry such as in packaging, identification cards, and labels, for example. It is useful to provide packaging which includes a security image invisible to a user under ambient conditions, but which can be rendered visible upon application of a stimulus; for example, if a customs and excise official wishes to check that imported goods are genuine goods or whether they are counterfeit goods. If the packaging includes the security image, rendered visible or detectable by suitable stimulus, the customs and excise official can determine that the packaging, and hence the goods, are not counterfeit. Likewise, it is advantageous to provide an identification card in which an image is invisible or a defined colour under ambient conditions, but which can be rendered visible or detectable, or change colour upon application of a stimulus in order to prove the identity of a user of the identity card, and in order to determine that the identity card is genuine and not a counterfeit identity card. There are many known examples of such security images, for example, in the applicant's co-pending applications PCT/GB2005/001763 and PCT/GB2005/001766.

In the manufacture of bank notes, it is desirable to include as many security features as possible, which may include multiple security images using a variety of compounds capable of changing colour upon application of a stimulus (including movement of the bank note to change viewing angle), or turning coloured from colourless, or vice versa.

In many countries, officials and state authorities use apparatus, such as third party verifiers, which detect the percentage light absorbance and/or reflection at a wavelength of approximately 800-900 nm (in the infrared region), to detect whether specific security images comprising compounds which absorb infrared radiation between 800-900 nm are present; and hence help to determine whether or not a bank note is genuine or counterfeit.

It is desirable to provide bank notes which contain security images comprising compounds capable of exhibiting 50% or less light reflectance at approximately 800-900 nm. Many bank notes include Carbon Black as a pigment which possesses the characteristic of less than 50% light reflectance at 800-900 nm. Unfortunately, in order to provide a suitably strong image, with the required light reflectance characteristics at 800-900 nm, Carbon Black is generally needed in a concentration which produces a dull grey image in the positions where the Carbon Black is located, when coated at concentrations generally used (for example, 3% w/w of the total weight of the ink dispersion laid down on the substrate paper for bank notes). Bank note counterfeiters recognise from the dull grey image that Carbon Black is present in bank notes, and commonly now use Carbon Black in order to avoid their counterfeit bank notes being detected as counterfeit when utilising third party verifiers to verify the light reflectance at 800-900 nm.

It would therefore be advantageous to provide a security image on a bank note or any other image article requiring a security image, in which a security image includes one or more compounds having a 50% or less light reflectance at 800-900 nm at a given concentration within an image (and preferably around 850 nm), and in which the compound utilised does not create a strongly coloured image. It would be particularly advantageous to provide such a compound for inclusion in a security image in which the compound produces a substantially colourless security image, but which has 30% or less light reflectance at 800-900 nm. Most preferably 10% light reflectance in the 800-900 region is desired.

It is therefore an aim of the preferred embodiments of the present invention to overcome or mitigate at least one problem with the prior art, whether expressly disclosed herein or not.

SUMMARY OF THE INVENTION

In Künstliche Organische Farbstoffe and Ihre Zwischenprodukte, Hans Rudolf Schweizer (Springer, Verlag 1964, pp 245-246), there is described a water soluble dye known as Naphthol Green B (C.I. Acid Green 1), useful in promoting the evaporation of water from sea-water to produce sea-salt—this works by enhanced heating through NIR absorption from solar radiation.

C.I. Acid Green 1 has the structure:

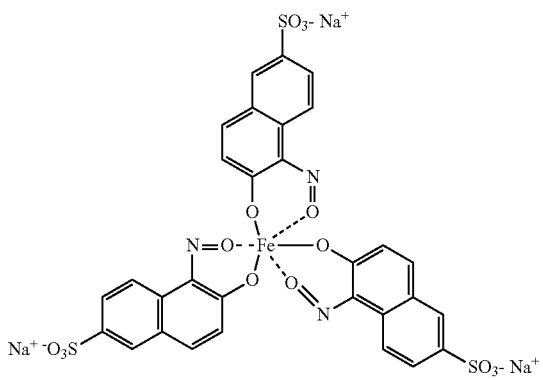

A commercially available pigment analogue of C.I. Acid Green 1 is C.I. Pigment Green 8 which has the structure:

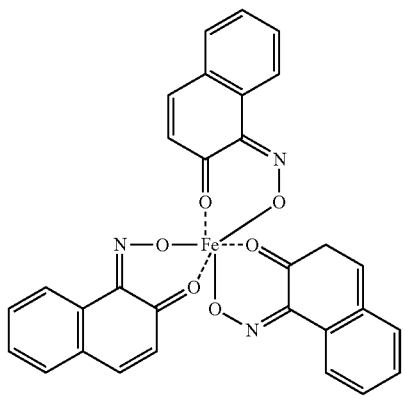

The applicant has surprisingly found that this green infrared-absorbing pigment can be coated in aqueous media, onto a suitable substrate in relatively low concentrations to produce a security image which exhibits less than 50% light reflectance at a wavelength of 800-900 nm, whilst exhibiting only a pale green colour on the substrate. The applicant further surprisingly found that similar pigments which include differing metal complexes and salts thereof, and polymers of the same, also exhibit light reflectance of less than 50% at a wavelength of 800-900 nm, whilst producing very pale, almost colourless images on substrates such as paper, card, and the like.

It should be noted that the iron ($Fe^{2+}$) complexes of o-nitroso naphthols or o-nitroso phenols are bright green, along with lanthanide complexes, where as cobalt complexes are brown. The colour thus varies with the choice of transition element.

Thus, image articles which include security images comprising C.I. Pigment Green 8 and similar compounds, exhibit excellent characteristics for security images on bank notes for detection by third party infrared verifiers, whilst being manageable, and able to be coated onto substrates from liquid medium.

Accordingly, in a first aspect of the present invention there is provided an image article comprising a substrate having a security image coated on at least a portion thereof, which security image effects less than 50% reflectance of radiation of a wavelength between 800 and 900 nm, wherein the security image comprises an infrared-absorbing compound selected from:

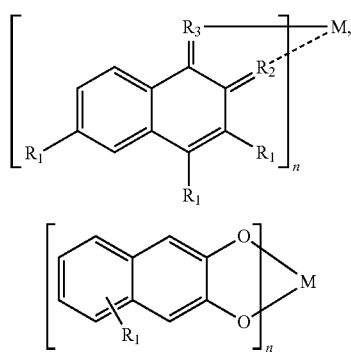

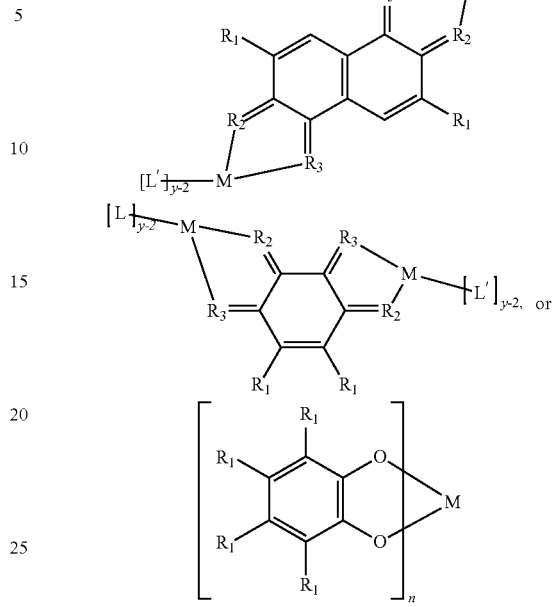

or a salt or polymer thereof, wherein
  M is a metal selected from a group 3-10 (Group IIIB-VIII) element or a lanthanide;
  $R_1$ is selected from hydrogen, phosphonate, sulphonate, nitro, halo, cyano, thiocyano, thioalkyl, thioaryl, alkyl, alkoxy, aryl, aryloxy, amines, substituted amines and substituted aryl;
  one of $R_2$ and $R_3$ is oxygen and the other of $R_2$ and $R_3$ is NO;
  n is a number corresponding to half the co-ordination number of the metal M;
  each L and L' is independently a ligand complexed to the metal M; and
  y is a number corresponding to the co-ordination number of the metal M;
wherein said infrared-absorbing compound does not create a strongly coloured security image.

The the image article of the present invention comprises a security image which is not strongly coloured. By this it is meant that the image itself is not strongly coloured: the compound used to form the image may in fact be strongly coloured when provided in concentrated form, but the amount applied to the substrate results in a security image which is not strongly coloured.

Suitably the security image is not brightly-coloured. Preferably it is pale, lightly coloured or colourless.

Preferably the infrared-absorbing compound of the security image is applied at concentrations such that the image formed has low absorption of light in the visible range, for example at 400 to 700 nm. Preferably the security image formed from the infra-red absorbing compound has a reflectance of greater than 50% at wavelengths of 400 to 700 nm.

Because the security image formed from the infra-red absorbing compound is not strongly coloured, it may be difficult to observe with the naked eye and/or may be masked by a further image at the same location which is more strongly coloured. This further image may overlap with some or all of the security image and may or may not be identical with said security image.

The security image may therefore be regarded as a hidden or covert image.

According to a second aspect of the present invention there is provided a method of manufacturing an image article comprising the steps of:

(a) providing a substrate; and
(b) image-wise coating a compound selected from:

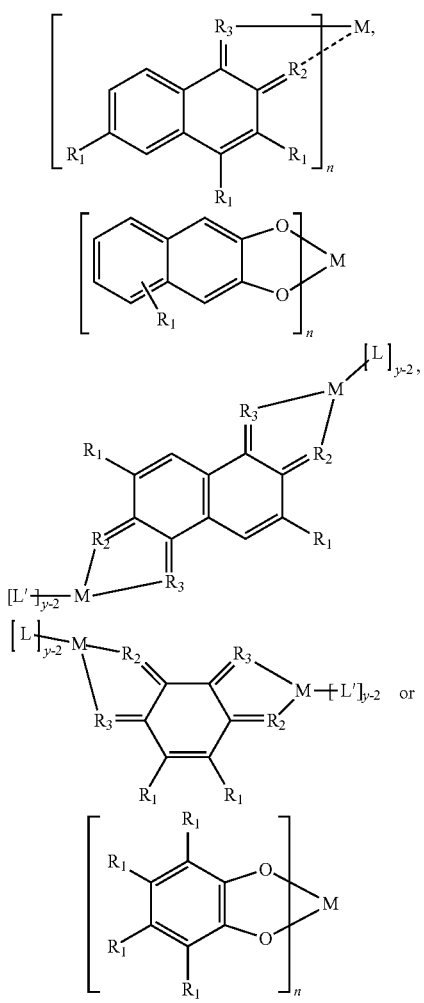

or a salt or polymer thereof, onto at least a portion of the substrate to form a security image which is not strongly coloured and which effects less than 50% reflectance of radiation of a wavelength between 800 and 900 nm, wherein:

M, $R_1$, $R_2$, $R_3$, n, L, L' and y are as described for the first aspect of the invention.

Suitably, M is selected from iron, cobalt, nickel, aluminium, scandium, chromium, vanadium, titanium, manganese or a lanthanide. Most preferably, M is selected from iron, cobalt and lanthanum.

Preferably, M is a metal having a co-ordination number of 6 or 8, and n is correspondingly 3 or 4, and y is correspondingly 6 or 8.

Preferred salts of the compounds coated onto the substrate in the first and second aspects of the invention include compounds of formula:

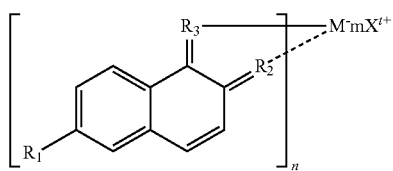

wherein M, n and $R_1$, $R_2$ and $R_3$ are as described for the first and second aspects of the invention, X is a metal cation selected from a group 1 or 2 metal (alkali metal and alkaline earth metal) and aluminium, and the sum of m and t correspond to the total number of negative charges on the compound.

Particularly preferred salts include those of formula:

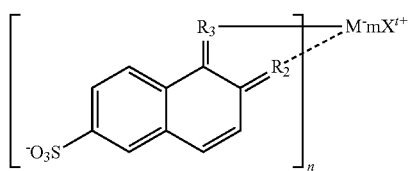

wherein M, X, n, m and t are as described herein above.

Particularly preferred salts include those having the following formulae:

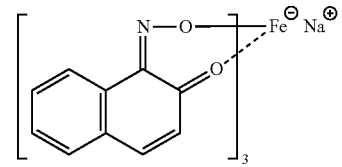

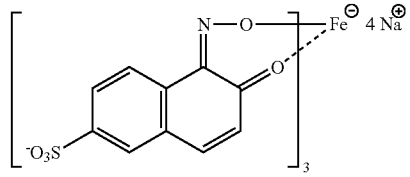

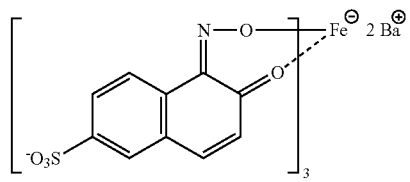

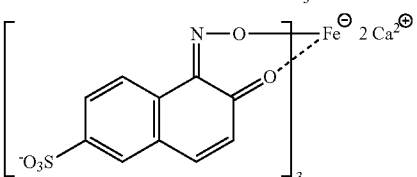

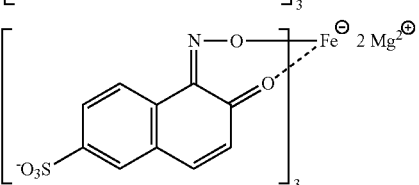

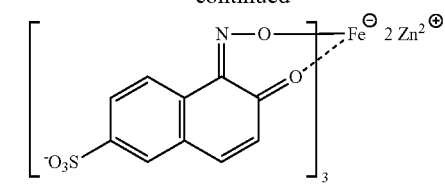

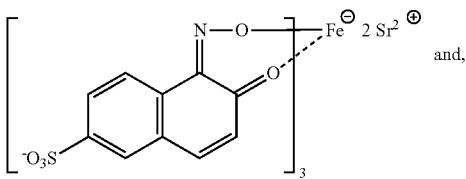

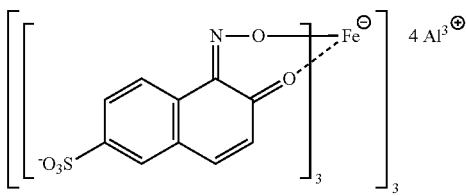

Each L and/or L' is preferably independently selected from chlorine, bromine, hydroxyl, water or pairs of ligands of group L and/or group L' may comprise a single ligand forming a ring structure with metal M, and may for example be formed from 1,3-dinitroso-2,4-dihydroxybenzene or 1,5-dinitroso-2,6-dihydroxy-naphthalene groups connected to the metal M via the nitroso and hydroxyl groups.

In particularly preferred embodiments, the compound of the security image coated onto the substrate has the formula:

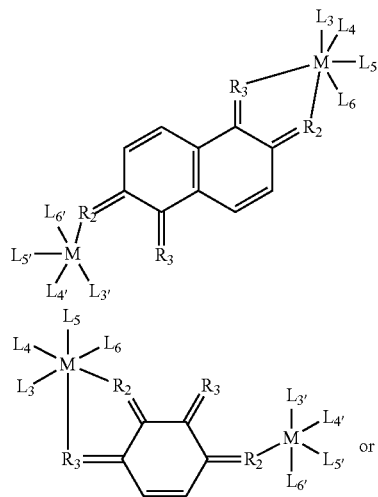

wherein M, $R_2$ and $R_3$ are as described herein above, L1-L6 and L1'-L6' are ligands independently selected from chlorine, bromine, hydroxyl, water, or any number of pairs of L3-L6 and/or L3'-L6' may be combined of a single ligand forming a ring structure with metal M, and may for example be formed from 1,3-dinitroso-2,4-dihydroxybenzene, or 1,5-dinitroso-2,6-dihydroxynaphthalene, connected to the metal M via the nitroso and hydroxyl groups.

Polymers of the infrared-absorbing compounds are preferably dendritic polymers in which each M is complexed to three dinitroso-2,4-dihydroxybenzene or three dinitroso-2,6-dihydroxynaphthalene groups (preferably 1,3-dinitroso-2,4-dihydroxybenzene, 1,5-dinitroso-2,6-dihydroxynaphthalene or 1,5-dihydroxy-4,8-dinitrosonaphthalene).

Particularly preferred polymeric forms of infra-red absorbing compound useful for the invention are:

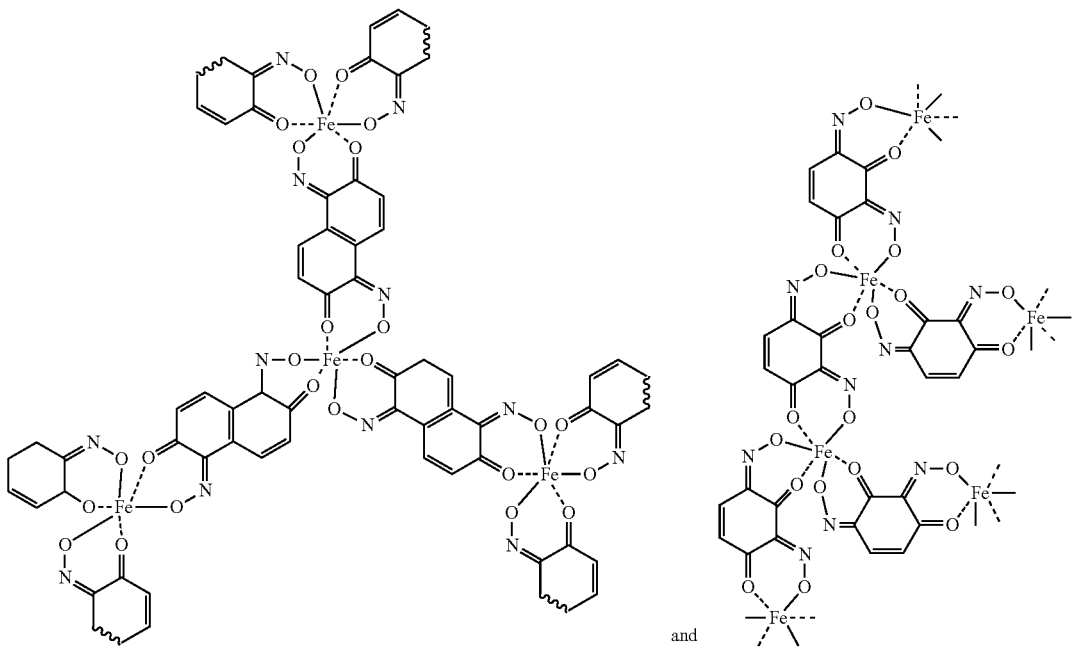

and wherein Fe may be replaced with any other metal M as described for the first or second aspects of the invention.

Suitably, the infrared-absorbing compound is image-wise coated onto the substrate in solution, or as a suspension or dispersion of the infrared-absorbing compound in a suitable medium.

Preferably the infrared-absorbing compound is coated onto the substrate in a composition further comprising one or more further pigments and/or one or more dyes. The composition containing the infrared-absorbing compound and one or more further pigments or dyes may comprise a solution of the one or more further pigments and/or dyes in which is dispersed the infrared-absorbing compound, a suspension or dispersion of the one or more further pigments and/or dyes and the infrared-absorbing compound, or any other suitable form.

Suitably the infrared-absorbing compound is coated onto the substrate as a dispersion or suspension of the infrared-absorbing compound, with or without further pigments and/or dyes, in a liquid medium. Intaglio ink bases commonly use tung oil, whilst the offset and letterpress ink bases commonly use linseed oil, an aromatic free mineral oil (boiling range 280-310° C.) and/or an aromatic free mineral oil (boiling range 260-290° C.), as liquid carriers. Tolvene, xylene or methylethylketone may also be used, for example.

Suitably the composition containing the infrared-absorbing compound is coated onto the substrate at a concentration of at least 1 gm$^{-2}$ (preferably at least 1 μm wet film thickness), more preferably at least 2 gm$^{-2}$ (preferably at least 2 μm wet film thickness), yet more preferably at least 4 μm$^{-2}$ (preferably at least 4 μm wet film thickness), and especially at least 6 gm$^{-2}$ (preferably at least 6 μm wet film thickness). Films ranging from 2 μm to 80 μm wet film thickness are used in the bank note industry. Preferably the infrared-absorbing compound is coated onto the substrate in an amount capable of absorbing greater than 50% of infrared radiation impinged or impinging on the substrate, more preferably greater than 75%. The use of further pigments and/or dyes which in themselves do not absorb and/or reflect infrared radiation at 800-900 nm helps to mask any colour formed by the infrared-absorbing compound when coated onto a substrate, and thus mask the presence of the infrared-absorbing compound from would-be counterfeiters.

Suitably the infrared-absorbing compound is coated onto the substrate as a dispersion in a dye- or pigment-containing ink, the ink preferably containing at least one oil as the medium in which the infrared-absorbing compound and/or further pigments or dyes in the ink are dispersed. Suitable oils include natural oils such as linseed oil, and synthetic hydrocarbon or mineral oils.

Suitably the infrared-absorbing compound is coated onto the substrate in a composition at a concentration which results in an image which is not strongly coloured. In some embodiments, the infrared-absorbing compound may be applied at concentrations of less that 4 wt %, for example approximately 1 wt % or 2 wt %.

The infrared-absorbing compound may be included in an ink composition which has a substantially identical colour to a second ink composition which does not contain the infrared-absorbing compound. To prepare such a combination of ink compositions (as a matched colour pair), the infrared-absorbing compound is added to a base ink formulation which results in a composition of a defined colour. The colour of a second portion of the base ink formulation is then adjusted (for example by the addition of known pigments) such that it is visually identical with the defined colour of the ink composition containing the infrared-absorbing material. Thus when the two compositions are applied to a substrate, the resultant images are visually indistinguishable with the naked eye.

The two ink compositions may be used to form a single image, part of the image being printed with the ink composition containing the infrared-absorbing compound and the remainder being printed with its matched colour pair ink. When viewed using an infrared camera only the part of the image containing the infrared-absorbing compound is seen.

Preferable substrates include paper, especially paper used for bank notes such as velin paper, card, metals (including alloy), textiles (including wool, cotton, hemp, jute, linen and flax, as natural textiles, and nylon, rayon, polyamide and polyester as synthetic textiles), rubber, ceramics, glass, composite materials, carbon fibre, and any mixture thereof.

Especially preferred substrates are paper and card, and most especially paper, such as velin paper, commonly used as bank note substrates.

Preferably the substrate is a sheet substrate and more preferably a substantially planar sheet substrate. The sheet substrate may be rigid or flexible, but is preferably flexible. The infrared-absorbing compound may be image-wise coated on one or both sides of the sheet substrate.

Preferably the image article is a printed article, suitably a paper article, which is printed on both sides.

Preferably it is printed with a coloured ink on both sides. It may be image-wise coated with the infrared-absorbing compound to form a security image on one or both sides.

There may be more than one infrared-absorbing compound coated onto the sheet substrate, and each infrared-absorbing compound may be coated simultaneously or sequentially.

The image article may comprise packaging, for example a pharmaceutical carton, an article of clothing, a label or the like. It may comprise an identification document, for example an identification card, a passport or driving licence. The image article may comprise a credit card, a voucher or a ticket, for example a cinema or theatre ticket, or airline or train ticket.

The image article may be of monetary value. It may for example be a share certificate, or a stamp certificate or tax voucher (for example a vehicle tax disc).

In some embodiments the image article may comprise one or more additional security elements. For example it may comprise one or more further security images. These security images may comprise compounds detectable by infrared radiation or may comprise compounds which are detectable by other types of radiation, for example ultraviolet or visible radiation.

Alternatively and/or additionally the one or more additional security elements may be selected from a hologram, a metallic strip running through the substrate, a watermark or an embossed portion.

The image article may include, as security features, intaglio printing, microprinting, a background image or red or green phosphors.

In especially preferred embodiments, the image article includes, as security elements, a mixture of covert and overt features. Overt features are those which may be detected by visible inspection of the article, for example the inclusion of a background image. Covert features include those which may be detected in response to a stimulus, for example the application of ultraviolet or infrared light.

Most preferably the image article is a banknote.

In preferred embodiments the security image of the image article of the present invention is suitable for inclusion as a security feature on a banknote.

Thus the infrared compound of the security image of the image article of the present invention typically exhibits good light-fastness. Preferably it exhibits good wash fastness. Preferably it exhibits good solvent fastness. Preferably the infrared compound of the security image of the present invention exhibits sufficient light-fastness and wash-fastness for it to be suitable for inclusion in a banknote.

There are typically 22 fastness tests that a banknote may be subjected to in order to determine the suitability of any security features present. These include chemical fastness to the following solvents: xylene, hydrochloric acid, sodium hydroxide solution, tetrachloroethylene.

To assess the suitability of an image article of the present invention for use as a banknote, the infrared absorbance of the security image may be measured and then the image article is immersed at room temperature in a beaker of the appropriate solvent for 30 minutes. The image article is removed, dried and its infrared absorbance re-measured. Any change in absorbance is then rated on a scale of 0-4, 4 being no change and 0 representing a substantial (greater than 50%) change.

The image article may also be subjected to conventional laundering wash-fastness tests and also light-fastness tests. For the wash-fastness test, the infrared absorbance of the security image of the image article is measured and then it undergoes a domestic home washing test cycle in which it is washed in a suitable detergent solution. After washing, the infrared absorbance of the security image of the image article is re-measured and any change in absorbance is again rated on a suitable scale.

The light-fastness test involves subjecting the image article to accelerated light fading in a xenon light chamber. The infrared absorbance of the security image of the image article is measured and it is then placed in a xenon light chamber along with a series of 8 blue wool standards and exposed to xenon light. The infrared absorbance of the security image is determined as each blue wool standard fades. The light-fastness is rated as the highest blue wool standard at which no significant change in infrared absorbance is noted. Blue wool standard 8 represents the highest level of light-fastness, whilst 1 represents the lowest level. A security image suitable for use on a bank note has a blue wool standard of at least 4.

Preferably the security image of the image article of the composition of the present invention exhibits a light-fastness which is equivalent to at least blue wool standard 5, more preferably at least blue wool standard 6.

According to a third aspect of the present invention there is provided use of a compound of formula:

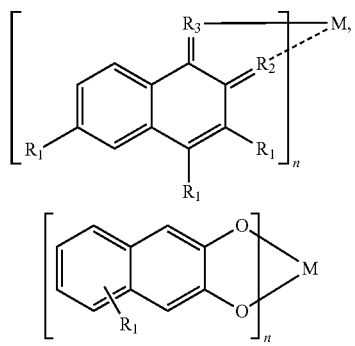

-continued

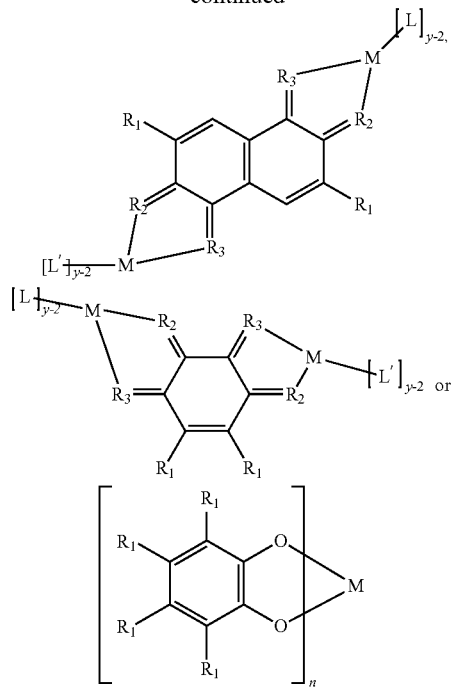

or a salt or polymer thereof, coated on at least a portion of the substrate, as an infrared radiation-absorbing additive in a security image coated on a substrate of an image article, wherein:

M is a metal selected from a group 3-10 (Group IIIB-VIII) element or a lanthanide;

$R_1$ is selected from hydrogen, phosphonate, sulphonate, nitro, halo, cyano, thiocyano, thioalkyl, thioaryl, alkyl, alkoxy, aryl, aryloxy, amines, substituted amines and substituted aryl;

one of $R_2$ and $R_3$ is oxygen and the other of $R_2$ and $R_3$ is NO;

n is a number corresponding to half the co-ordination number of the metal M;

each L and L' is independently a ligand complexed to the metal M; and y is a number corresponding to the co-ordination number of the metal M;

wherein said security image is not strongly coloured.

Suitably the infrared absorbing compound, coating, substrate and image article are as described for the first aspect of the invention.

According to a fourth aspect of the present invention there is provided a method of verifying the authenticity of an image article of the first aspect, the method comprising exposing said image article to radiation having a wavelength of between 800 and 900 nm, and measuring the reflectance of said radiation.

For an authentic image article, the reflectance in the region of the security image is suitably less than 50%.

The method of the fourth aspect may be carried out using any suitable detector. One suitable device is a Shimadzu UV-3101 PC UV-VIS-NIR scanning spectrophotometer. An infrared camera could also be used.

Typically radiation is applied and the reflectance thereof is measured, thus allowing absorbance to be calculated. Preferably the method of the fourth aspect employs a reader device. The reader device may comprise an infrared emitter and an infrared detector.

The method may further comprise measuring the extent of the absorption of infrared radiation at a selected wavelength. Thus the percentage absorbance or reflectance can be measured.

The method of the fourth aspect of the present invention may in some embodiments permit a quick, non-quantitative determination of the presence or otherwise of an infrared-absorbing material, by quickly checking for broadband adsorption or absorption at specific wavelength.

Alternatively, the method may be used to measure quantitatively the extent of absorbance at a specific wavelength. The more accurately the infrared absorption spectrum of an article can be measured, the more difficult it would be to counterfeit such an article.

The reader device could be built into a machine, for example a passport scanner, a chip-and-pin device, or an ATM. Alternatively a reader device could be supplied independently as a mobile device. The reader device may for example be provided as a hand held pen type detection device which would offer a pass/fail response on scanning a sample.

The method of the fourth aspect may be carried out periodically on randomly selected articles or it may be carried out routinely on every article. For example, a photosensitive diode could be included in a cash machine to measure the IR absorbance at a given wavelength of each banknote. Thus, a counterfeit banknote could be easily detected.

EXAMPLES

For better understanding of the various aspects of the invention and to show how embodiments of the same may be put into effect, the invention will now be described by way of the following non-limiting examples.

Example 1

A green infrared-absorbing pigment (Pigment Green B, CI Pigment Green 8) was synthesised in accordance with the following procedure; the structure of the pigment being given below in

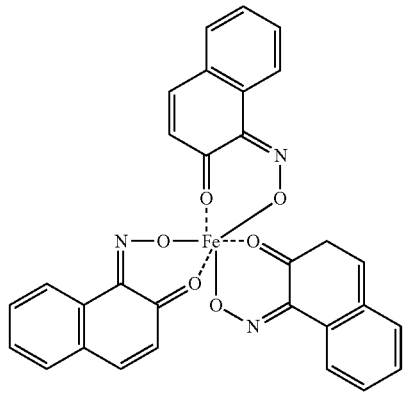

2-Naphthol (10 g, 0.07M) was dissolved in a warm solution of sodium hydroxide (2.8 g, 0.07M) in distilled water (120 ml). The solution was cooled to 0-5° C. and sodium nitrite (5 g, 0.073M) was added. The solution was stirred and 5.6M sulphuric acid (17 ml) was slowly added over 90 minutes; the solution being kept at 0-5° C. throughout the addition of the acid. The solution was stirred for a further 1 hour after the addition of the acid was complete, after which time sodium metabisulphite (13.3 g, 0.07M) was added and the suspension stirred until the nitroso compound had completely dissolved to yield a green solution; the solution being stirred for a further 30 minutes after which time the pH of the solution was adjusted to 6.5. A solution of iron II sulphate heptahydrate (6.4 g, 0.023M) in distilled water (10 ml) was added, followed by a small amount of sodium hydroxide solution to yield a green precipitate. The precipitate was stirred for 30 minutes and then collected by filtration. The precipitate was washed thoroughly with distilled water and finally dried in a vacuum desiccator. The iron II complex was purified by dissolving it in a minimum amount of dimethylformamide, filtering the solution to remove any solid and finally precipitating the iron II complex via the addition of water. The green iron II complex (Pigment Green B) was collected by filtration and dried in a vacuum desiccator.

Example 2

The process described in Example 1 was repeated, but in this case cobalt II chloride hexahydrate (5.5 g, 0.023M) was added in place of the iron II sulphate heptahydrate to yield the brown cobalt complex.

Example 3

The process described in Example 1 was repeated, but in this case lanthanum III chloride hexahydrate (8.6 g, 0.023M) was added in place of the iron II sulphate heptahydrate to yield the light green lanthanum complex.

Example 4

The process described in Example 1 was repeated, but in this case aluminium potassium sulphate dodecahydrate (10.9 g, 0.023M) was added in place of the iron II sulphate heptahydrate to yield the green aluminium complex.

Example 5

The process described in Example 1 was repeated, but in this case resorcinol (7.7 g, 0.07M) was used in place of 2-naphthol to yield a dendritic polymeric green iron complex; the pigment being fast to washing and light and sold commercially as Solid Green 0. The structure of the 3:1 polymeric iron complex is given below.

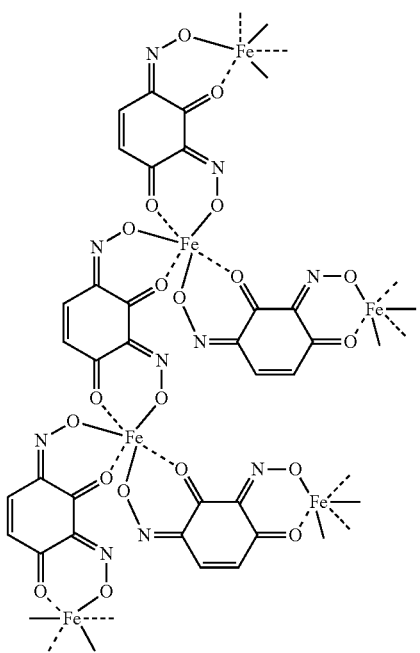

Example 6

A further polymeric green infrared-absorbing pigment was synthesised via the nitrosation of 2,6-dihydroxynaphthalene with nitrous acid and its subsequent complexation with iron. Thus, 2,6-dihydroxynaphthalene (2.8 g, 0.018M) was dissolved in a warm solution of sodium hydroxide (5.6 g, 0.036M) in distilled water (40 ml). The solution was cooled to 0-5° C. and sodium nitrite (2.5 g, 0.036M) was added. The solution was stirred and 5.6M sulphuric acid (9 ml) was slowly added over 90 minutes; the solution being kept at 0-5° C. throughout the addition of the acid. The solution was stirred for a further 1 hour after the addition of the acid was complete, after which time sodium metabisulphite (6.84 g, 0.036M) was added and the suspension stirred until the nitroso compound had completely dissolved to yield a green solution; the solution being stirred for a further 30 minutes after which time the pH of the solution was adjusted to 6.5. A solution of iron II sulphate heptahydrate (1.67 g, 0.006M) in distilled water (10 ml) was added, followed by a small amount of sodium hydroxide solution to yield a green precipitate. The precipitate was stirred for 30 minutes and then collected by filtration. The precipitate was washed thoroughly with distilled water and finally dried in a vacuum desiccator. The polymeric iron II complex was purified by dissolving it in a minimum amount of dimethylformamide, filtering the solution to remove any solid and finally precipitating the iron II complex via the addition of water. The iron II complex was collected by filtration and dried in a vacuum desiccator. The structure of the green polymeric iron II complex formed is given below:

Example 7

Naphthol Green B (CI Acid Green 1) is a water-soluble sulphonated derivative of Pigment Green B which can be readily converted to a water-insoluble pigment via conversion to its strontium, calcium, barium, magnesium, aluminium or zinc salt. The structure of Naphthol Green B is given below:

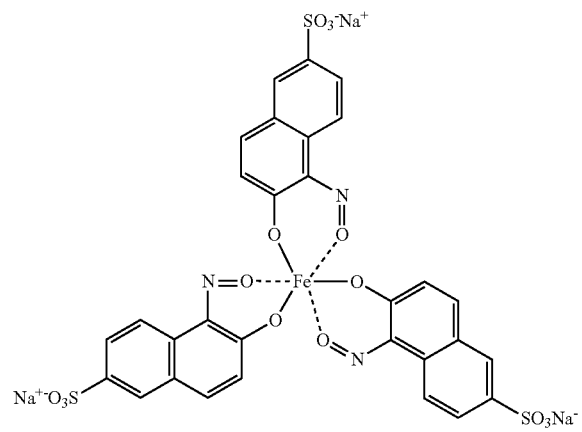

Alternatively some authors (Zollinger, Color Chemistry, Syntheses, Properties, and Applications of Organic Dyes and Pigments, 3$^{rd}$ Edition, Wiley-VCH, 2003) write the structure of this dye as:

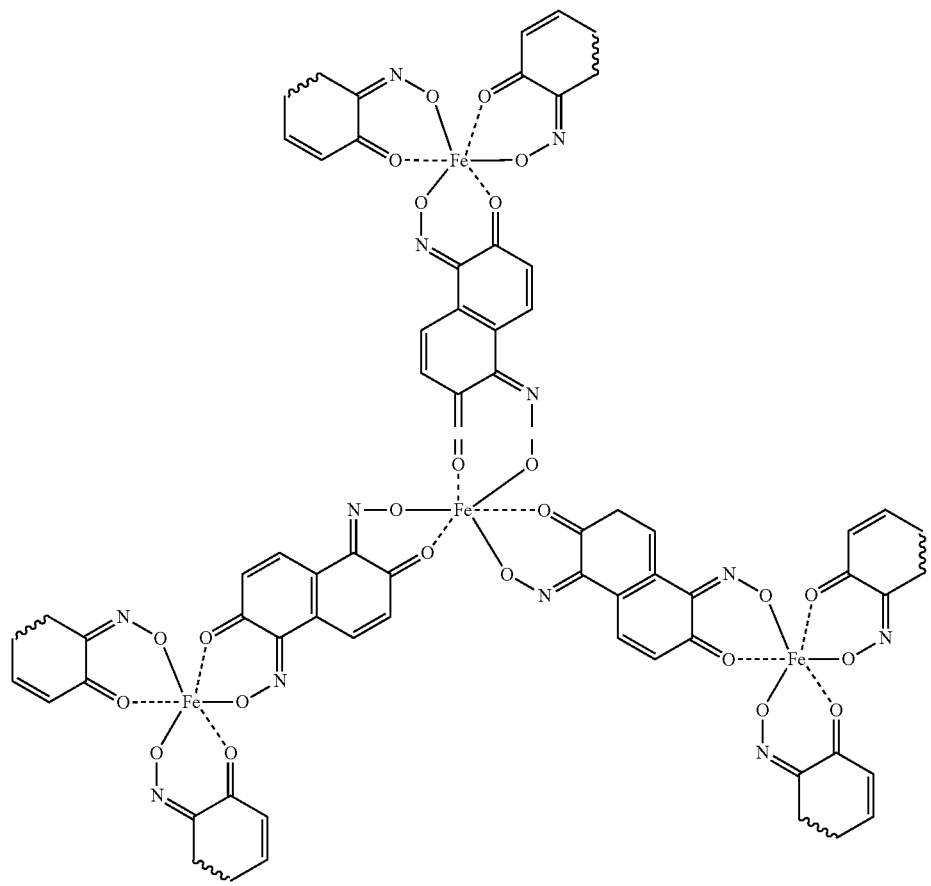

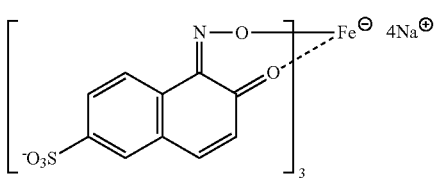

Thus, Naphthol Green B (4.4 g) was dissolved in distilled water (75 ml) and heated at 35° C. An alkaline solution of rosin, prepared by dissolving rosin (0.83 g) and sodium hydroxide (0.3 g) in distilled water (30 ml) at 50° C., and an aqueous solution of barium chloride, prepared by dissolving barium chloride dihydrate (4.0 g) in distilled water (30 ml), were simultaneously added to the stirred dye solution at 35° C. The dye solution was raised to the boil and boiled for 10 minutes, after which time cold distilled water (100 ml) was added to cool the pigment suspension. The precipitated green barium pigment was collected by filtration, washed thoroughly with cold distilled water and then dried in a vacuum desiccator overnight.

Example 8

The process described in Example 7 was repeated, but in this case calcium chloride hexahydrate (4.0 g) was used in place of barium chloride dihydrate to precipitate the dye as a water-insoluble green pigment.

Example 9

The process described in Example 7 was repeated, but in this case strontium chloride hexahydrate (4.0 g) was used in place of barium chloride dihydrate to precipitate the dye as a water-insoluble green pigment.

Example 10

The process described in Example 7 was repeated, but in this case magnesium chloride hexahydrate (4.0 g) was used in place of barium chloride dihydrate to precipitate the dye as a water-insoluble green pigment.

Example 11

The process described in Example 7 was repeated, but in this case zinc acetate dihydrate (4.0 g) was used in place of barium chloride dihydrate to precipitate the dye as a water-insoluble green pigment.

Example 12

The process described in Example 7 was repeated, but in this case aluminium potassium sulphate dodecahydrate (4.0 g) was used in place of barium chloride dihydrate to precipitate the dye as a water-insoluble green pigment.

Example 13

An intaglio security ink was prepared by dispersing an infrared-absorbing pigment in a commercially available intaglio ink formulation. Thus, the infrared-absorbing pigment (0.5 g) synthesised in Example 1 was dispersed in a yellow intaglio ink base (24.5 g) (Gleitsmann Security Inks GmbH) on a triple roll mill; the intaglio ink base being formulated as follows in Table 1:

TABLE 1

| Intaglio ink base formulation | |
|---|---|
| Component | Weight (%) |
| Modified vehicle* | 38.0 |
| Pigment | 2.0 |
| Calcium carbonate | 49.6 |
| Polyethylene wax (micronised) | 8.0 |
| Drier (10% manganese octoate) | 0.3 |
| Drier (18% cobalt octoate) | 0.1 |
| Aliphatic mineral oil (boiling range 170-260° C.) | 2.0 |

*The modified vehicle was composed of a commercial vehicle/varnish (80%), Trionol HK 9 (Lawter International, Belgium) and bodied tung oil (20%).

Proof prints of the intaglio infrared-absorbing security ink were prepared on velin paper using a Prüfbau proof printer; the inks being printed at a film thickness of 90.0 gm$^{-2}$. The IR absorbance of the resulting print was measured on a Shimadzu UV-3101 UV-VIS-NIR spectrophotometer incorporating a reflectance head attachment; the print exhibiting an IR absorbance of 94.2% at a wavelength of 800 nm.

Example 14

A letter-press security ink was prepared by dispersing an infrared-absorbing pigment in a commercially available letter-press ink formulation. Thus, the infrared-absorbing pigment (0.5 g) synthesised in Example 1 was dispersed in a yellow letter-press ink base (24.5 g) (Gleitsmann Security Inks GmbH) on a triple roll mill; the letter-press ink base being formulated as follows in Table 2:

TABLE 2

| Intaglio ink base formulation | |
|---|---|
| Component | Weight (%) |
| Varnish* | 63.5 |
| Pigment | 4.5 |
| Calcium carbonate | 22.3 |
| Linseed oil | 5.1 |
| Aliphatic mineral oil (boiling range 260-310° C.) | 4.0 |
| Hydroquinone | 0.3 |
| Drier (10% manganese octoate) | 0.2 |
| Drier (18% cobalt octoate) | 0.1 |

*The varnish was composed of a modified phenolic resin (40%), linseed oil (20%), aromatic free mineral oil (boiling range 280-310° C.) (20%), aromatic free mineral oil (boiling range 260-290° C.) (19.3%) and aluminium (ethylacetoacetonato) isopropoxide (0.7%).

Proof prints of the letter-press infrared-absorbing security ink were prepared on velin paper using a Prüfbau proof printer; the inks being printed at a film thickness of 4.0 gm$^{-2}$. The IR absorbance of the resulting print was measured on a Shimadzu UV-3101 UV-VIS-NIR spectrophotometer incorporating a reflectance head attachment; the print exhibiting an IR absorbance of 61.3% at a wavelength of 800 nm.

Example 15

An offset security ink was prepared by dispersing an infrared-absorbing pigment in a commercially available offset ink formulation. Thus, the infrared-absorbing pigment (1.0 g) synthesised in Example 1 was dispersed in a yellow offset ink base (24.0 g) (Gleitsmann Security Inks GmbH) on a triple roll mill; the offset ink base being formulated as follows in Table 3:

TABLE 3

Intaglio ink base formulation

| Component | Weight (%) |
|---|---|
| Varnish* | 67.0 |
| Pigment | 4.5 |
| Calcium carbonate | 9.2 |
| Linseed oil | 13.7 |
| Polyethylene wax | 5.0 |
| Hydroquinone | 0.3 |
| Drier (10% manganese octoate) | 0.2 |
| Drier (18% cobalt octoate) | 0.1 |

*The varnish was composed of a modified phenolic resin (40%), linseed oil (20%), aromatic free mineral oil (boiling range 280-310° C.) (20%), aromatic free mineral oil (boiling range 260-290° C.) (19.3%) and aluminium (ethylacetoacetonato) isopropoxide (0.7%).

Proof prints of the offset infrared-absorbing security ink were prepared on velin paper using a Prüfbau proof printer; the inks being printed at a film thickness of 2.0 gm$^{-2}$. The IR absorbance of the resulting print was measured on a Shimadzu UV-3101 UV-VIS-NIR spectrophotometer incorporating a reflectance head attachment; the print exhibiting an IR absorbance of 62.5% at a wavelength of 800 nm.

Example 16

The process described in Example 15 was repeated, but in this case the IR absorber synthesised in Example 2 (2.5 g) was used instead of that synthesised in Example 1. Prüfbau proof prints were prepared at a film thickness of 6.0 gm$^{-2}$; the prints exhibiting an IR absorbance of 46.2% at a wavelength of 800 nm.

Example 17

The process described in Example 15 was repeated, but in this case the IR absorber synthesised in Example 3 (1.25 g) was used instead of that synthesised in Example 1. Prüfbau proof prints were prepared at a film thickness of 6.0 gm$^{-2}$; the prints exhibiting an IR absorbance of 19.2% at a wavelength of 800 nm.

Example 18

The process described in Example 15 was repeated, but in this case the IR absorber synthesised in Example 4 (1.25 g) was used instead of that synthesised in Example 1. Prüfbau proof prints were prepared at a film thickness of 6.0 gm$^{-2}$; the prints exhibiting an IR absorbance of 35.7% at a wavelength of 800 nm.

Example 19

The process described in Example 15 was repeated, but in this case the IR absorber synthesised in Example 5 (0.5 g) was used instead of that synthesised in Example 1. Prüfbau proof prints were prepared at a film thickness of 2.0 gm$^{-2}$; the prints exhibiting an IR absorbance of 59.8% at a wavelength of 800 nm.

Example 20

The process described in Example 15 was repeated, but in this case the IR absorber synthesised in Example 6 (2.5 g) was used instead of that synthesised in Example 1. Prüfbau proof prints were prepared at a film thickness of 6.0 gm$^{-2}$; the prints exhibiting an IR absorbance of 47.8% at a wavelength of 800 nm.

Example 21

The process described in Example 15 was repeated, but in this case the IR absorber synthesised in Example 7 (2.5 g) was used instead of that synthesised in Example 1. Prüfbau proof prints were prepared at a film thickness of 6.0 gm$^{-2}$; the prints exhibiting an IR absorbance of 92.4% at a wavelength of 800 nm.

Example 22

The process described in Example 15 was repeated, but in this case the IR absorber synthesised in Example 8 (2.5 g) was used instead of that synthesised in Example 1. Prüfbau proof prints were prepared at a film thickness of 6.0 gm$^{-2}$; the prints exhibiting an IR absorbance of 63.3% at a wavelength of 800 nm.

Example 23

The process described in Example 15 was repeated, but in this case the IR absorber synthesised in Example 9 (2.5 g) was used instead of that synthesised in Example 1. Prüfbau proof prints were prepared at a film thickness of 6.0 gm$^{-2}$; the prints exhibiting an IR absorbance of 61.3% at a wavelength of 800 nm.

Example 24

The process described in Example 15 was repeated, but in this case the IR absorber synthesised in Example 10 (2.5 g) was used instead of that synthesised in Example 1. Prüfbau proof prints were prepared at a film thickness of 6.0 gm$^{-2}$; the prints exhibiting an IR absorbance of 77.3% at a wavelength of 800 nm.

Example 25

The process described in Example 15 was repeated, but in this case the IR absorber synthesised in Example 11 (2.5 g) was used instead of that synthesised in Example 1. Prüfbau proof prints were prepared at a film thickness of 6.0 gm$^{-2}$; the prints exhibiting an IR absorbance of 63.5% at a wavelength of 800 nm.

Example 26

The process described in Example 15 was repeated, but in this case the IR absorber synthesised in Example 12 (k.5 g) was used instead of that synthesised in Example 1. Prüfbau proof prints were prepared at a film thickness of 6.0 gm$^{-2}$; the prints exhibiting an IR absorbance of 59.7% at a wavelength of 800 nm.

Example 27

The process described in Example 1 was repeated, but in this case 1-naphthol was used instead of 2-naphthol a water-insoluble green pigment; the structure of the pigment being given below:

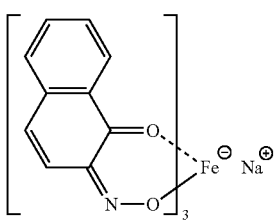

Example 28

The process described in Example 15 was repeated, but in this case the IR absorber synthesised in Example 26 (1 g) was used instead of that synthesised in Example 1. Prüfbau proof prints were prepared at a film thickness of 2.0 gm$^{-2}$; the prints exhibiting an IR absorbance of 61.5% at a wavelength of 800 nm.

Example 29

A 3:1 iron complex of 2,3-dihydroxynaphthalene was synthesised via the following process. 2,3-Dihydroxynaphthalene (0.0051M, 0.82 g) (Aldrich) was dissolved in methanol (50 ml) and gradually added to a solution of iron II sulphate heptahydrate (0.0017M, 0.5 g) (Aldrich) in distilled water (50 ml). The solution was heated to the boil for 5 minutes to yield a navy blue/black pigment. The pigment was collected by filtration, washed thoroughly with cold water and dried in a vacuum desiccator. The structure of the pigment is given below:

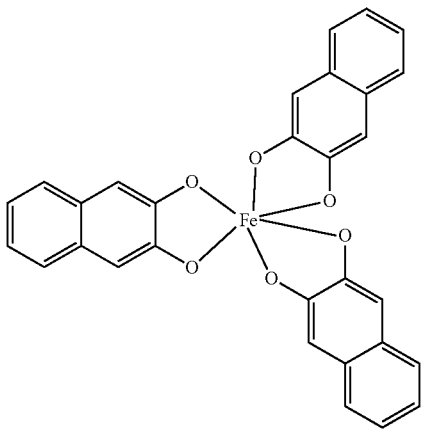

Structure of the 3:1 iron complex of 2,3-dihydroxynaphthalene

Example 30

The process described in Example 15 was repeated, but in this case the IR absorber synthesised in Example 29 (1 g) was used instead of that synthesised in Example 1. Prüfbau proof prints were prepared at a film thickness of 6.0 gm$^{-2}$; the prints exhibiting an IR absorbance of 59.2% at a wavelength of 800 nm.

Example 31

Colour pairs were prepared with the following ink compositions by shading the base ink colour to match the colour of the ink obtained after the addition of Pigment Green B.

| Base ink | Image colour | Pigment Green B (%) added to base ink | IR reflectance (%) between 800-840 nm |
| --- | --- | --- | --- |
| IR Transparent white | Pale green | 5 | 40 |
| IR Transparent white | Light green | 10 | 28 |
| IR Transparent white | Green | 15 | 23 |
| Base Ink 680141 | Greenish-blue | 12 | 27 |
| Base Ink 680150 | Bluish-green | 12 | 20 |
| Base Ink 680102 | Yellowish-green | 12 | 25 |
| Base Ink 680101 | Green | 12 | 27 |

Example 32 (Comparative)

Aminium dyes: Water-soluble cationic dyes were converted to water-insoluble pigments by complexation with phosphotungstic acid. The parent dyes, A191, A192 and A207 were supplied by Gentex Optics Inc (USA). However, their maximum IR absorbance occurred between 900-1200 nm and so was outside the desired absorption band of 800-900 nm. The pigments are darkly coloured blues and greens, and produce strongly coloured prints even at low concentrations. They also failed to meet the chemical resistance requirements, the complexes being destroyed in sodium hydroxide solution.

Example 33 (Comparative)

Polycylic vat dyes: Water-insoluble dyes such as Cibanon Green BF-MD, CI Vat Green 1 (Ciba) and Cibanon Blue BOA-01, CI Vat Blue 20, (Ciba) exhibited suitable light-fastness and chemical resistance fastness properties, but failed to achieve acceptable IR absorbance over the 800-900 nm band required. They are also highly coloured, and as relatively high concentrations must be used to achieve the desired IR absorption characteristics, strongly coloured image areas are produced.

Example 34 (Comparative)

Cyanine dyes: Water-soluble soluble cationic dyes were converted to water-insoluble pigments by complexation with phosphotungstic acid. The parent dyes, IR-792 perchlorate and dimethyl{4-[1,5,5-tris(4-dimethylaminophenyl)-2,4-pentadienylidene]-2,5-cyclohexadien-1-ylidene}ammonium perchlorate were supplied by Aldrich (UK). These dyes offered suitable characteristics, but suffered from poor light-fastness properties, Blue Wool Standard 3 compared with a Blue Wool Standard of at least 6 for Pigment Green B.

Example 35 (Comparative)

Squarilium dyes: A colourless water-soluble anionic dye was converted to a water-insoluble pigment by forming its calcium, barium or strontium lakes. The dye used was a research sample synthesised in the Department of Colour and Polymer Chemistry, University of Leeds. This dye was chosen because of its colourless nature and strong IR absorption characteristics. However, the water-insoluble lakes of this particular squarilium dye failed to offer suitable IR characteristics over the desired 800-900 nm range.

The invention claimed is:

1. A method of verifying the authenticity of an image article, the method comprising exposing said image article to radiation having a wavelength of between 800 and 900 nm, and measuring the reflectance of said radiation; wherein the image article comprises a substrate having a security image coated on at least a portion thereof, which security image effects less than 50% reflectance of radiation of a wavelength between 800 and 900 nm, wherein the security image comprises an infrared-absorbing compound selected from:

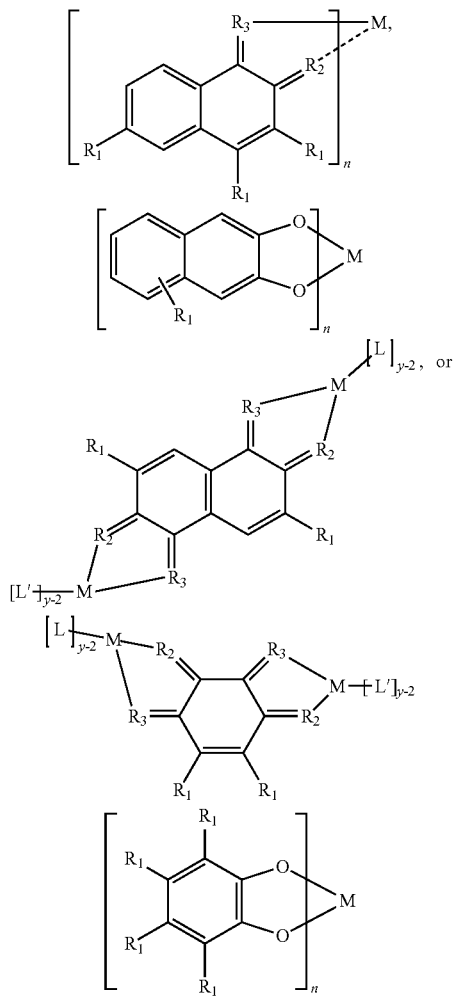

or a salt or polymer thereof, wherein
M is a metal selected from a group 3-10 (Group IIIB-VIII) element or a lanthanide;
R1 is selected from hydrogen, phosphonate, sulphonate, nitro, halo, cyano, thiocyano, thioalkyl, thioaryl, alkyl, alkoxy, aryl, aryloxy, amines, substituted amines and substituted aryl;
one of R2 and R3 is oxygen and the other of R2 and R3 is NO;

n is a number corresponding to half the co-ordination number of the metal M;

each L and L' is independently a ligand complexed to the metal M; and y is a number corresponding to the co-ordination number of the metal M;

wherein said infrared-absorbing compound does not create a strongly coloured security image.

2. An method according to claim 1 wherein M is selected from iron, cobalt and lanthanum.

3. A method according to claim 1 wherein the infrared absorbing compound is a salt of formula:

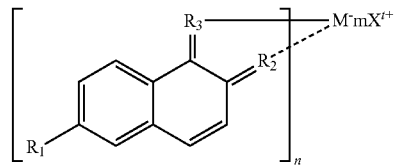

wherein M, n and R1, R2 and R3 are as defined in claim 1, X is a metal cation selected from a group 1 or 2 metal and aluminium, and the product of m and t corresponds to the total number of negative charges on the compound.

4. A method according to claim 3 wherein the salt is selected from:

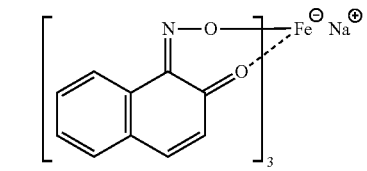

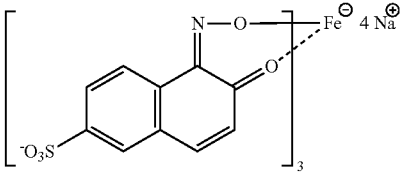

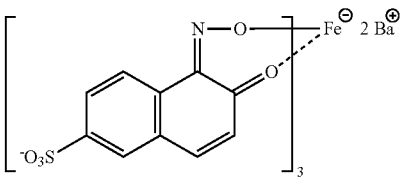

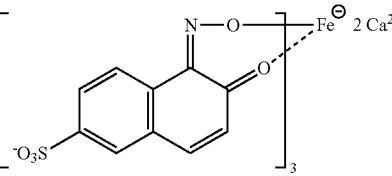

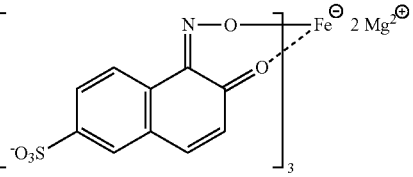

-continued

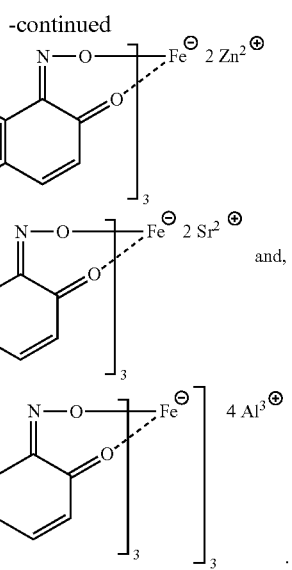

and,

5. A method according to claim 1 wherein the security image is pale, lightly coloured or colourless.

6. A method according to claim 1 wherein the security image formed from the infra-red absorbing compound has a reflectance of greater than 50% at wavelengths of 400 to 700 nm.

7. A method according to claim 1 wherein the security image further comprises one or more additional security elements.

8. A method according to claim 1 wherein the security image includes covert and overt security elements.

9. A method according to claim 1 wherein the image article is a bank note.

10. A method according to claim 1 which employs a reader device comprising an infrared emitter and an infrared detector.

11. A method according to claim 1 which further comprises measuring the extent of the absorption of infrared radiation at a selected wavelength.

* * * * *